US00PP18920P3

(12) United States Plant Patent
Parham

(10) Patent No.: US PP18,920 P3
(45) Date of Patent: Jun. 10, 2008

(54) ***CHRYSANTHEMUM* PLANT NAMED 'OMEGA TIME DARK PINK'**

(50) Latin Name: *Chrysanthemum morifolium*
Varietal Denomination: Omega Time Dark Pink

(75) Inventor: Ruth Parham, Bognor Regis (GB)

(73) Assignee: Cleangro Ltd, Chichester, West Sussex (GB)

( * ) Notice: Subject to any disclaimer, the term of this patent is extended or adjusted under 35 U.S.C. 154(b) by 0 days.

(21) Appl. No.: 11/488,590

(22) Filed: Jul. 18, 2006

(65) Prior Publication Data

US 2007/0033689 P1 Feb. 8, 2007

Related U.S. Application Data

(60) Provisional application No. 60/703,359, filed on Jul. 28, 2005.

(51) Int. Cl.
*A01H 5/00* (2006.01)

(52) U.S. Cl. ..... Plt./297

(58) Field of Classification Search ..... Plt./297
See application file for complete search history.

(56) References Cited

U.S. PATENT DOCUMENTS 14,956 A1 6/2004 Redman ..... Plt./286
15,004 A1 7/2004 Redman ..... Plt./297

*Primary Examiner*—Annette H Para
(74) *Attorney, Agent, or Firm*—Winston & Strawn, LLP

(57) ABSTRACT

A new variety of *Chrysanthemum* plant named 'Omega Time Dark Pink', having dark pink single flowers with a green disc.

1 Drawing Sheet

Latin name of the genus and species: Botanical classification: *Chrysanthemum morifolium.*

Variety denomination: The new *Chrysanthemum* variety denomination is 'Omega Time Dark Pink'.

BACKGROUND OF THE INVENTION

The present invention comprises a new and distinct cultivar of *Chrysanthemum* botanically known as *Chrysanthemum morifolium,* and referred to by the cultivar name 'Omega Time Dark Pink'.

'Omega Time Dark Pink', identified as 20929-19 was discovered as a naturally occurring whole plant mutation in a controlled cultivated planting of the variety 'Mega Time Rose' (U.S. Plant Pat. No. 15,004).

The new variety 'Omega Time Dark Pink' has been asexually reproduced by vegetative cuttings in Chichester, West Sussex, United Kingdom and the distinguishing characteristics are retained through successive generations of asexual reproduction.

BRIEF SUMMARY OF THE INVENTION

'Omega Time Dark Pink' is a pot type of *Chrysanthemum* plant variety having dark pink single flowers with a green disc.

Comparison with Original Cultivar

Plants of the new *Chrysanthemum* variety 'Omega Time Dark Pink' are similar to the original cultivar 'Mega Time Rose' in plant habit and growth rate. In side-by-side comparisons in Chichester, West Sussex, United Kingdom, under commercial practice, plants of the new *Chrysanthemum* variety 'Omega Time Dark Pink' compared to plants of the original cultivar 'Mega Time Rose' in the following characteristics:

1. The new variety 'Omega Time Dark Pink' produces dark pink single flowers whereas the original cultivar 'Mega Time Rose' produces pink single flowers.
2. Plants of the new variety 'Omega Time Dark Pink' have the same sized inflorescence as plants of the original cultivar 'Mega Time Rose'.

Comparison with 'Hi Time'

Plants of the new *Chrysanthemum* variety 'Omega Time Dark Pink' are dissimilar to plants of the variety 'Hi Time' (U.S. Plant Pat. No. 14,956) in plant habit and growth rate. However, in side-by-side comparisons in Chichester, West Sussex, United Kingdom, under commercial practice, plants of the new *Chrysanthemum* variety 'Omega Time Dark Pink' differed from plants of 'Hi Time' in the following characteristics:

1. The new variety 'Omega Time Dark Pink' produces dark pink single flowers whereas 'Hi Time' produces dark pink purple single flowers.
2. Plants of the new variety 'Omega Time Dark Pink' have larger and taller inflorescence than plants of 'Hi Time'.
3. Plants of the new variety 'Omega Time Dark Pink' have a slower response than plants of 'Hi Time'.

BRIEF DESCRIPTION OF ILLUSTRATIONS

Typical specimens of the plant and flowers for the new *Chrysanthemum* variety 'Omega Time Dark Pink' are shown in the accompanying digital photograph. The colors shown are as true as possible within the usual limits of this kind of illustration.

FIG. 1 is a whole plant view of the new variety 'Omega Time Dark Pink' grown in a pot.

The plant shown in the illustration and described below is 56 days from the onset of Short Days.

DETAILED BOTANICAL DESCRIPTION

The following description of the new *Chrysanthemum* variety 'Omega Time Dark Pink' is of plants grown in a greenhouse in Chichester, West Sussex, United Kingdom, in the month of October. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 2,500 Lux. The plants respond well to the use of growth retardant, such as one B9 treatment at about 2 grams per liter. To produce a commercial product, the plants may be pinched once with the center bud removed. The typical container size for commercial growth is 1 liter. It has been observed that the shelf life of the new variety is about 28 days with a response time of about 7.5 weeks. The new variety is suitable for growth in a temperature range of 15° C. to 25° C.

The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 24.
Width (cm): 30.
Stem:
- *Length* (*cm*).—5.5.
- *Diameter* (*cm*).—0.5.
- *Texture.*—Slightly pubescent.
- *Color.*—138A.

Branching characteristics: Upright and free branching.
Lateral branches:
- *Length* (*cm*).—14.
- *Diameter* (*cm*).—0.4.
- *Texture.*—Slightly pubescent.

Number of breaks from pinch: 6.
Response time: 52 days.
Vigor: Medium/Tall.
Shelf life: 28 days.
Life of blooms: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings. The plants were grown for two weeks in Long Day conditions (20 hours of light) and then transferred to Short Day conditions (13 hours of dark).

Propagation:
- *Type.*—Vegetative propagation via stem cuttings.
- *Time to rooting.*—14 days with soil temperatures of 18° C.
- *Rooting habit.*—After 7 Long Days, the first roots emerge and form root primordia. In 14 Long Days, a complete root system is developed.

Foliage

Number of leaves per lateral branch: 12.
Compound or single: Single.
Arrangement of leaves: Alternate.
- *Shape of leaf.*—Typically 5 lobed.
- *Size of leaf.*—Width (cm): 5.5. Length (cm): 8.5.
- *Leaf apex.*—Acute.
- *Base.*—Obtuse.
- *Attachment.*—Petioled.
- *Aspect: Slightly undulating.*
- *Margin.*—Palmately lobed.
- *Surface characteristics.*—Top: Slightly pubescent. Bottom: Pubescent.

Petiole:
- *Color.*—137D.
- *Length* (*cm*).—1.5.
- *Diameter* (*cm*).—0.4.
- *Surface.*—Slightly pubescent.

Venation: Net, prominent lateral and mid-veins at underside.
- *Color.*—Upper side: 138B. Under side: 138B.

Color:
- *Mature leaf, upper side.*—137B; under side: 138A.
- *Young leaf, upper side.*—137B; under side: 138A.

Flower

Flower appearance: Matte.
Flower type: Single.
Flower form: Slightly cupped.
Flower shape: Circular.
Flowering habit: Cyme.
Number of blossoms per branch: 6.
Typical and observed flowering season: January to December.
Inflorescence form: Cyme.
- *Depth of fully expanded blossoms* (*cm*).—2.
- *Diameter of fully expanded blossoms* (*cm*).—7.

Phyllaries:
- *Number.*—20.
- *Color.*—137C.
- *Length* (*cm*).—0.7.
- *Width* (*cm*).—0.2.
- *Texture/appearance.*—Pubescent.

Peduncle:
- *Length* (*cm*).—10.
- *Diameter* (*cm*).—0.4.
- *Angle from stem* (*degrees*).—10.
- *Color.*—137C.
- *Surface.*—Slightly pubescent.
- *Habit.*—Slightly undulating.
- *Strength.*—Strong.

Pedicel:
- *Length.*—Terminal (cm): 3; lateral (cm): 4.5.
- *Diameter* (*cm*).—0.2.
- *Color.*—137C.
- *Surface.*—Slightly pubescent.
- *Habit.*—Straight.
- *Strength.*—Moderate.

Ray florets:
*Form/shape.*—Straight with parallel edges to the central mid vein.
*Texture/appearance.*—Matte.
*Number per flower.*—25.
*Length* (*cm*).—3.5. Width (cm): 1.
*Apex.*—Rounded.
*Base.*—Tapered.
*Margin.*—Entire.
Disc florets:
*Form/shape.*—Cylindric.
*Texture/appearance.*—Shiny.
*Number per flower.*—Near 150.
*Length* (*cm*).—0.6. Width (cm): 0.1.
*Diameter of disc* (*cm*).—1.5.
Fragrance: None.
Flower bud (at onset of color):
*Length* (*cm*).—1.
*Diameter* (*cm*).—1.3.
*Form/shape.*—Globular.
General flower color:
1. *Ray florets, upper side.*—Immature: 67B. Mature: 64C. Older/Fading: 64D.
2. *Ray florets, under side.*—Immature: 64C. Mature: 63C. Older/Fading: 63C.
3. *Disc florets.*—Immature: 152C. Mature: 15C. Older/Fading: 15C.
4. *Bud.*—63C.

Flower progression with age: There is no change with the flower form but there is a slight color fading with age.

Reproductive Organs

Gynoecium present on Ray and Disc florets.

Ray florets per individual flower: Pistillate.
*Pistil number.*—25.
*Stigma color.*—154A.
*Stigma shape.*—Forked.
*Style color.*—154B.
*Style length* (*cm*).—0.3.
Disc florets per individual flower: Pistillate.
*Pistil number.*—150.
*Stigma color.*—154A.
*Stigma shape.*—Forked.
*Style color.*—154B.
*Style length* (*cm*).—0.3.
Androecium: Not observed.
Fruit and seeds: None observed.

What is claimed is:

1. A new and distinct variety of *Chrysanthemum* plant, substantially as described and illustrated herein.

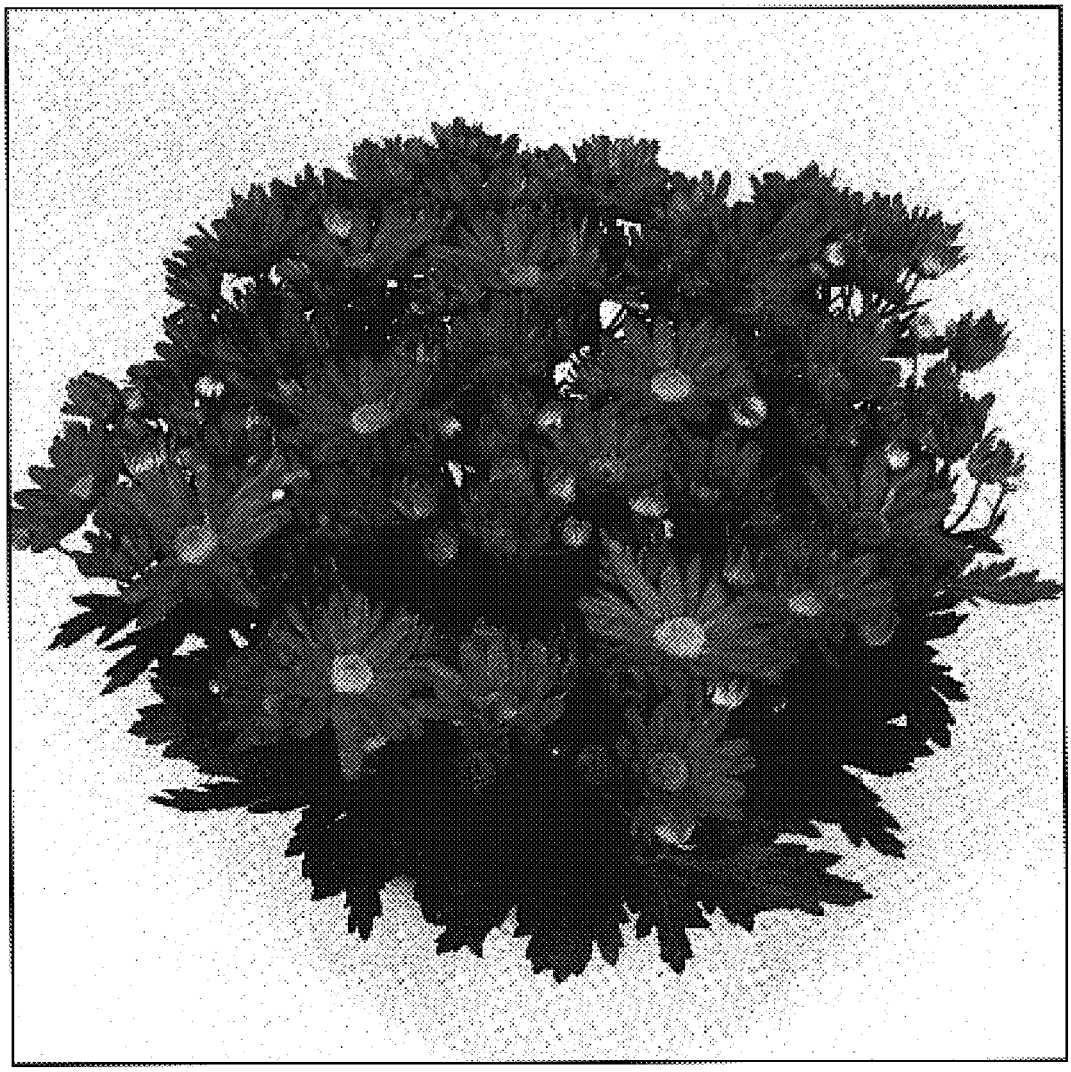

* * * * *